United States Patent
Flechsig et al.

(10) Patent No.: US 9,273,348 B2
(45) Date of Patent: Mar. 1, 2016

(54) METHOD AND ARRAY FOR THE REPLICATION AND ANALYSIS OF NUCLEIC ACIDS

(75) Inventors: Gerd-Uwe Flechsig, Teterow (DE); Joerg Peter, Kamenz (DE)

(73) Assignee: Universitaet Rostock, Rostock (DE)

( * ) Notice: Subject to any disclaimer, the term of this patent is extended or adjusted under 35 U.S.C. 154(b) by 2102 days.

(21) Appl. No.: 11/884,066

(22) PCT Filed: Feb. 10, 2006

(86) PCT No.: PCT/DE2006/000255
§ 371 (c)(1),
(2), (4) Date: Jun. 30, 2008

(87) PCT Pub. No.: WO2006/084457
PCT Pub. Date: Aug. 17, 2006

(65) Prior Publication Data
US 2008/0269066 A1    Oct. 30, 2008

(30) Foreign Application Priority Data

Feb. 11, 2005  (DE) .......................... 10 2005 007 148

(51) Int. Cl.
*C12Q 1/68*    (2006.01)
(52) U.S. Cl.
CPC .................................... *C12Q 1/6837* (2013.01)
(58) Field of Classification Search
None
See application file for complete search history.

(56) References Cited

U.S. PATENT DOCUMENTS

2007/0116444 A1*   5/2007  Brown .......................... 392/467

FOREIGN PATENT DOCUMENTS

| DE | 19960398 | 6/2001 |
|----|----------|--------|
| WO | WO-99/05321 | 2/1999 |
| WO | WO-02/099386 | 12/2002 |
| WO | WO-2005/098438 | 10/2005 |

OTHER PUBLICATIONS

Walker et al (1992 Nucleic Acids Research 20:1691-1696).*
Hassmann et al (2001 Biosensors & Bioelectronics 16:857-863).*
MJ Research PTC 200 manual downloaded Sep. 8, 2014.*
Gerd-Uwe Flechsig et al.; "DNA Hybridization Detection at Heated Electrodes"; Langmuir, vol. 21, No. 17, 2005, pp. 7848-7853.

* cited by examiner

*Primary Examiner* — Christopher M Gross
(74) *Attorney, Agent, or Firm* — Jordan and Hamburg LLP

(57) ABSTRACT

The invention includes a method and array for replicating and analyzing one or a plurality of different target sequences in nucleic acid samples. The different reactions for replicating the target sequences occur simultaneously on an array with selectively heatable array elements with their reaction surfaces, some of which have been modified differently, and in the sample solution disposed thereabove. The target sequences are analyzed using molecular detection on reaction surfaces of said array that have been modified with probe strands. The target strands are replicated and analyzed simultaneously, successively, or alternately.

8 Claims, 9 Drawing Sheets

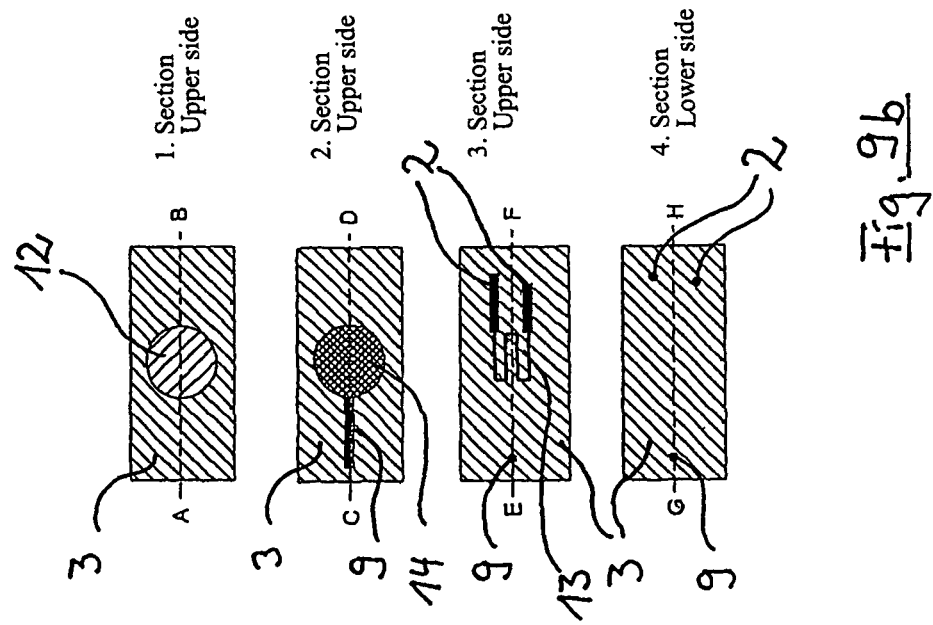
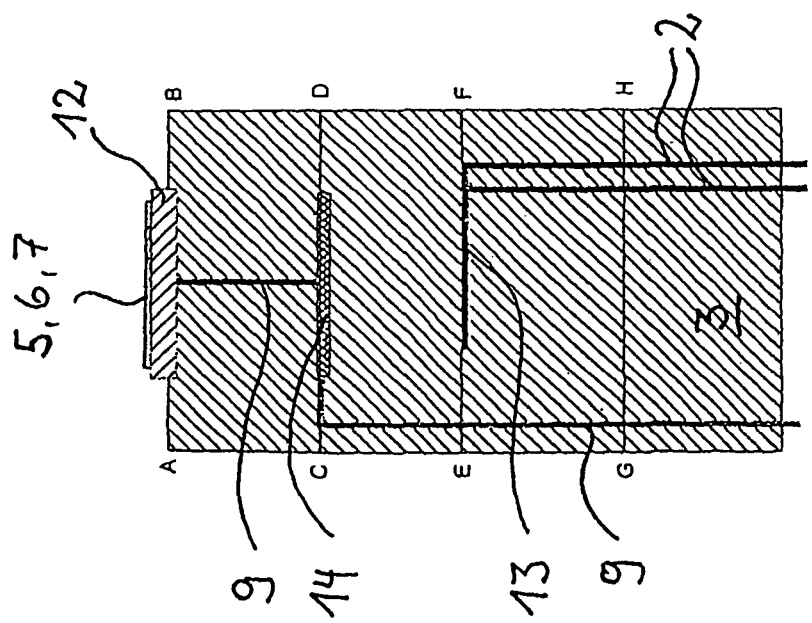
Fig. 9a
Fig. 9b

METHOD AND ARRAY FOR THE REPLICATION AND ANALYSIS OF NUCLEIC ACIDS

BACKGROUND OF THE INVENTION

The invention relates to a method for replicating and analyzing one or a plurality of different target sequences in nucleic acid sequences and apparatus including an array to be selectively heated for replicating and analyzing a plurality of target sequences in nucleic acid samples.

It is known that when analyzing nucleic acid sequences, the latter must almost always be multiplied because frequently too few copies of the nucleic acid sequences sought are present in the initial sample. In addition, selective reproduction of the sequences to be analyzed facilitates their detection in the presence of a great excess of other nucleic acid sequences.

Replication is generally performed using the polymerase chain reaction (PCR). For this, the complete sample solution is alternately heated and cooled cyclically in order to permit the steps of denaturing the double strand (approx. 95° C.), hybridizing the primer (e.g. 50° C.), and extending the primer (e.g. 75° C.) to run repeatedly one after the other.

So-called thermocyclers are commercially available for this purpose; these are devices in which the reaction is performed in small, typically 500-μL, reaction vessels. The reaction vessels can be combined to create palettes to enable parallel processing of a plurality of samples. Miniaturized analysis systems in which the PCR is performed are also described.

Kopp et al. describe a hydrostatically operated flow system with three different heated zones. A flow channel is configured such that it alternately passes through the three set temperature areas so that in this manner the temperature cycle is created for the PCR (M.U. Kopp, A.D. de Mello, A. Manz: "Chemical Amplification: Continuous-Flow PCR on a Chip", Science 280 (1198) 1046).

Z. Chen et al. provide a similar system, in this case the movement of the liquid being initiated by the thermosyphon principle (Z. Chen, S. Qian, W. R. Abrams, D. Malamud, H. H. Bau, Anal. Chem. 76 (2004) 3707).

Liu et al. describe a printed circuit board-based integrated analysis system that combines both sample preparation and DNA multiplication and microarray detection (R. H. Liu, J. Yang, R. Lenigk, J. Bonanno, P. Grodzinski: "Self-Contained, Fully Integrated Biochip for Sample Preparation, Polymerase Chain Reaction Amplification, and DNA Microarray Detection", Analytical Chemistry 76 (2004) 1824).

In the strand displacement amplification (SDA) method, cyclical heating and cooling of the sample are not needed. Special nick enzymes and primers at a constant temperature ensure that the double strands are separated by newly formed complementary strands and the old complementary strand is displaced (SDA with thermophilic enzymes, U.S. Pat. No. 5,648,211; SDA combined with bioelectronic chips U.S. Pat. No. 6,238,868 B1).

Fluorimetric analysis of the replicated target strands can be performed simultaneous to the PCR. In this real-time PCR, the nearly complete PCR process is not required, but rather it is possible to draw conclusions about the content of nucleic acids with the target sequence in the starting material just from the temporal course of the analysis signal.

The analysis of nucleic acids can also be performed on selectively heatable electro-chemical analysis arrays, such as are described in U.S. Pat. No. 6,255,677 B1 and DE application 10 2004 017750.

Also known are analysis systems in which both replication and also analysis occur on one array. U.S. Pat. No. 6,326,173 B1 and Nat. Biotechnol. 18 (2000) 199 describe e.g. electrically induced hybridization of the target with the primer. The primers can be dissolved homogeneously or immobilized. Replication occurs using SDA. Optical methods are used for the analysis.

Primarily the great degree of complexity in terms of time and equipment are disadvantageous in most of the known methods, as is the complicated technical operation. In addition, the replication step generally occurs separate from the analysis step in terms of both time and equipment.

For this reason widespread use of conventional DNA sequence analysis technology for instance in medicine has not been possible in the past.

In all of the previous PCR variants it has been a hindrance that all of the components for the PCR analysis solution must go through the entire temperature cycle. Therefore only certain thermally stable polymerases can be used for the primary extension, which increases costs and limits versatility. One alternative is to re-add the polymerase after each cycle, which is very inconvenient.

Otherwise the analysis is generally performed using optical methods that increase the complexity of the equipment, or using separating methods (electrophoresis) that do not permit parallel determination of a large number of different target sequences, or only permit it with difficulty.

However, a rapid and simple method for parallel determination of many target sequences (even in trace amounts) is desirable. A miniaturized analysis system with integrated PCR or SDA that permits determination of a plurality of target sequences would be very advantageous. For instance, individual therapy with targeted and sparing use of medications would be possible. Costs and side-effects could be reduced, and the success of therapy could be improved. Development of medications would also profit greatly from such a novel method because frequently gene expression must be monitored for testing new drugs.

SUMMARY OF THE INVENTION

The object of the invention is to make it possible to rapidly and simultaneously replicate and analyze a plurality of different target sequences in one nucleic acid sample using an apparatus having a monolithic array.

For this, a biochemical method and an array with reaction bottles that are to be heated selectively are to be created for replicating and analyzing nucleic acid sequences, whereby both the replication and the simultaneous electrochemical determination of a large number of nucleic acid sequences in a short period of time are to be enabled.

For performing the biochemical method of real-time PCR it is inventively provided that at least one heatable reaction surface of the array is embodied as a working electrode and is modified with probe strands in order to detect and bind the replicated target strands.

It has been proved advantageous that, for better fixation of the probe strands, the latter are preferably bonded with thiol linkers (sulfur groups) to the reaction surface, which can comprise for instance a layer of gold. The temperature is to be selected individually such that the highest possible stringency is attained and thus it is possible to differentiate between fully complementary and incorrect target strands.

At least one other unmodified reaction surface on the array should be brought to a temperature, preferably to greater than 90° C., at which the double strands are separated.

In one preferred embodiment, at least one other reaction surface is provided that is provided with polymerase molecules and that is brought to a discrete temperature. In the case of the Taq polymerase, which is generally used, a temperature between 50 and 70° C. has proved particularly advantageous. However, other types of polymerases can also be used, in particular those that actually work at room temperature and do not tolerate high temperatures.

The polymerase is preferably bonded to the reaction surface using thiol linkers (sulfur groups). Because of this the polymerase reaction is localized at this solid phase and can proceed undisturbed at the temperature set. It has proved advantageous to embed the polymerase in a gel layer on the reaction surface of the array element.

The polymerase can also be fixed using avidin-biotin complexes. Moreover, immobilization can occur using hydroxyl, amino, carboxyl, or carboxylate groups. As an alternative to the metal or carbon surface, silicon or silicate-containing materials and organic polymers can be used as the substrate for the polymerase modification in the case of indirect heating of the reaction surface because these embodiments of the reaction surfaces are not based on directly heatable array elements and therefore no electrical heating current flows through and thus no heating current flows through them and they therefore do not have to be electrically conductive.

The convection in the sample solution over the individual heated reaction surfaces and the arranged cooling body ensures continuous mixing of the sample volume. The mixing of the entire sample volume, which mixing is forced by the convection, can be facilitated by the surface of the cooling body being in an inclined position relative to the surface of the array. Then there is a wedge-shaped space for the sample solution between array and cooling body. The angle of the surface of the cooling body to the surface of the array is up to 30°, but it has been demonstrated that it should preferably not exceed 20°.

For supporting mixing of the entire volume of the sample, the apparatus made of array and cooling body as a whole can also be positioned on an incline so that the surface of the array leaves the horizontal and assumes an angle. In an extreme case the angle can be up to 90°, the space between the surface of the array and the cooling body then being in a vertical position. In this position the individual convection streams that occur at each individual array element overlap to an even greater extent the overall convection stream that passes through the entire volume. When the space for the sample volume is in the vertical position, essentially only an overall convection stream occurs that rises on the heated array and flows back downward on the cooling body.

It has been demonstrated that the individual different array elements can inventively also be arranged multiply in so-called groups. All reaction surfaces modified with polymerase, all reaction surfaces modified with probe strands, and all reaction surfaces for thermal denaturation then each form one group. The arrangement of the individual reaction surfaces can be different as a group.

It has been demonstrated that it is advantageous when the surface area of the reaction surfaces modified with probe strands is small compared to that of the enzyme-modified reaction surfaces. Because the reaction surfaces modified with the probe strands should bind the target strands, which also act as a template for the replication, however.

Because of this the reaction surfaces modified with probe strands compete with the enzyme-modified reaction surfaces for the target strands. In order to suppress this competition in the initial phase of the reaction, the temperature of the reaction surfaces modified with the probe strands can initially be set high enough that no target strands adhere. Once the replication has progressed, their temperature would be lowered individually such that then the target strands are thermally stringently bonded.

It is advantageous that in contrast to the conventional PCR technique, the cyclical heating and cooling does not come about in that the temperature of the entire sample volume is set each time. On the contrary, due to the convective movement the individual nucleic acid molecules travel in the liquid with the sample medium via the heated reaction surfaces and the bottom of the cooling body alternately into areas with high or low temperature. The convection also ensures intensive material transport of the dissolved substances involved (e.g. the nucleotides). This sharply accelerates the desired replication process. The reaction surfaces with the probe strands continuously capture the produced target strands.

Using electroanalytic methods such as e.g. amperometry, chronocoulometry, voltammetry, and potentiometry, it is therefore possible to track the progress of the replication in real time, with the advantages of real time PCR (shorter duration of analysis, possibility of determining concentration).

The inventive performance of the replication of the target sequences by strand displacement amplification (SDA) permits the replication processes to unfold in homogenous solution. As heatable working electrodes, the reaction surfaces of the array elements are thereby connected to an electrochemical measuring device and embodied such that their temperature can be individually controlled and with their probe sequences they can be individually modified.

This permits the replication reaction to be tracked electrochemically in real time. Using convection in the solution located over them, the hot working electrodes ensure rapid transport of the target strands formed and thus ensure rapid hybridization with the immobilized probe strands. In this case, as well, the reaction surfaces modified with probe strands compete for target strands with the polymerase molecules.

In order to suppress this competition in the initial phase of the reaction, during SDA as well the temperature of the reaction surfaces modified with the probe strands can initially be set high enough that no target strands adhere. Once the replication has progressed, their temperature would be lowered individually such that then the target strands are thermally stringently bonded.

In one embodiment for SDA at least one additional heated array element is provided, the reaction surface of which is modified with the polymerase. Because of this the polymerase reaction can be performed at its own temperature, regardless of the temperature in the sample solution.

The reaction surfaces of the array elements preferably comprise an arrangement of electrically conductive layers of a desired thickness, in particular made of carbon, platinum, palladium, gold, iridium, bismuth, cadmium, nickel, zinc, silver, copper, iron, lead, aluminum, manganese, mercury, or alloys thereof, which are advantageously produced as planar substrates by sputtering or vapor deposition on an electrically non-conductive substrate material such as e.g. glass or glass-like substances, ceramic, various types of polymers, etc.

The production of layer-like conductive array elements is not limited solely to sputtering or vapor deposition; rather, it has been demonstrated that the array elements can also be produced on the substrate galvanically or by appropriate arrangement of thin metal wires, bands, or the like. Heatable carbon array elements can be created in particular by screen printing, as pastes made of carbon powder or glassy carbon in the form of layers and rods.

Each individual array element on the substrate possesses at each end an electrical heating current contact for feeding current and can be heated electrically. The heating current lines at the individual array elements can be created in different ways.

In one embodiment, the heating current lines on the array element are guided through the substrate from below. However, it is also possible to guide the heating current lines in the same plane as the array element to the edge of the array. Both variants, even coupled, are possible and shall not limit the invention.

However, it is also possible to arrange a third contact on the array element. With this so-called center contact, the reaction surfaces of the individual array elements can be connected as working electrodes to an electrochemical measuring device (galvanostat, potentiostat, current meter, voltammeter). This so-called symmetrical heatable electrode enables simultaneous electrical heating with alternating current and electrochemical measuring, without the heating current disturbing the electrochemical signals, which are smaller by several orders of magnitude.

For heating the individual reaction surfaces of the array elements, a common heating current can be supplied e.g. via a transformer as current source. The voltage and current strength applied to the array elements are measured separately at each array element and the values found are forwarded to the associated regulator. Each regulator is itself connected to the associated actuator (e.g. an electronic resistance) that influences the current strength that is to be fed to the array element. Thus it is possible to precisely regulate the temperature of each individual array element and thus of each individual reaction surface. Therefore all external influences that would lead to temperature fluctuations in the array elements can be compensated.

Individual disturbance to the temperature of the array elements is also taken into account.

Corresponding to the circuit, a desired number of array elements can be switched together as groups.

However, it is also possible to control the temperature of the individual array elements globally using their reaction surfaces on the entire array in that the current for the entire array is adjusted by means of an actuator (e.g. an electrical resistance). This is less complex because it is a single-channel system. External disturbances that would lead to uniform temperature fluctuations on the entire array can also be compensated in this simpler manner.

In this simple form the individual temperature for the individual reaction surfaces is specified in that, in addition to the basic setting and control of the entire array by a central actuator, a (where required electronic) trimmer resistor is arranged upstream of each individual array element.

In this case, as well, the array can be supplied with current e.g. via a transformer. The temperature is determined using at least one temperature sensor that is arranged on the array on or between the reaction surfaces and the temperature value is forwarded to the central control unit that influences at least one actuator (e.g. an electronic resistance) for the entire system. Thus a certain current strength that is required for heating the reaction surfaces is centrally set and controlled.

Thus it is possible to control the temperature of the array elements and their reaction surfaces individually, but to control the temperatures set for the entire array centrally.

For indirect heating of the array elements, generally both direct current and alternating current are suitable. The heaters can all be connected to the current supply via a common ground connection.

For direct heating of the array elements, only high frequency alternating current, preferably greater than 1 kHz, preferably e.g. 100 kHz, is suitable for avoiding undesired polarization effects and thus undesired secondary reactions on the reaction surface.

In addition, for the groups of reaction surfaces for thermal denaturation and reaction surfaces modified with polymerase, for supplying heating current all affected array elements can be contacted via a common ground connection in the case of direct heating.

For the group of individually and directly heated array elements and their reaction surfaces modified with probe strands, special precautions must be taken because as working electrodes for electrochemical measurement these must be galvanically separated from one another.

The individual array elements are supplied or not supplied with current, and thus also separated from one another if simultaneous heating and measurement is not desired, via multiple double switches, depending on the setting of the circuit. For simultaneous electrochemical measurement and electrical heating, all heated and all array elements used as working electrodes must be galvanically separated from one another. This can be done using individual transformers.

A cooling element, preferably comprising aluminum or copper, is arranged over the array such that the liquid is enclosed with the sample medium in a thin layer between array and cooling element. The thickness of the layer is preferably only a few µm, but it can also be larger. The bottom of the cooling element can be flat. However, it preferably possesses a structure for deflecting the connective flows in the sample solution so that global mixing of the entire sample solution is supported. These structures can be embodied for instance as knobs or channel-like depressions.

Advantageously, the surface of the cooling element that faces the sample solution, and that can be flat or slightly structured, is arranged opposing the surface of the array on a slight upward or downward incline so that a wedge-shaped layer occurs along the longitudinal axis of the sample medium. Then, a global convection stream forms in the wedge-shaped layer, and it mixes all of the sample solution and overlaps the local convection streams that are over each heated array element. The cooling element can be connected for instance to a passive, appropriately dimensioned ribbed cooling body or can be identical thereto. For greater quantities of heat or if the initial temperature of the sample solution is supposed to be below room temperature, a Peltier element can also be connected to the cooling element or identical thereto.

The planar surface of the cooling element that is in contact with the sample solution is preferably coated with an inert gold or platinum layer. The cooling element can also be used as a common counterelectrode due to the large surface area. A silver/silver chloride electrode arranged on the array can advantageously be used as a common reference electrode.

Additional advantages, details, and inventive features result from the examples in the following detailed descriptions of the invention using the attached drawings.

BRIEF DESCRIPTION OF THE DRAWINGS

FIG. 9a is a sectional, detailed view of the measuring electrode with indirect heating;

FIG. 9b is a detailed view of individual layers (levels) of the measurement electrode.

DETAILED DESCRIPTION OF THE INVENTION

Identical parts are provided with the same reference numbers in the following.

Figure 1:
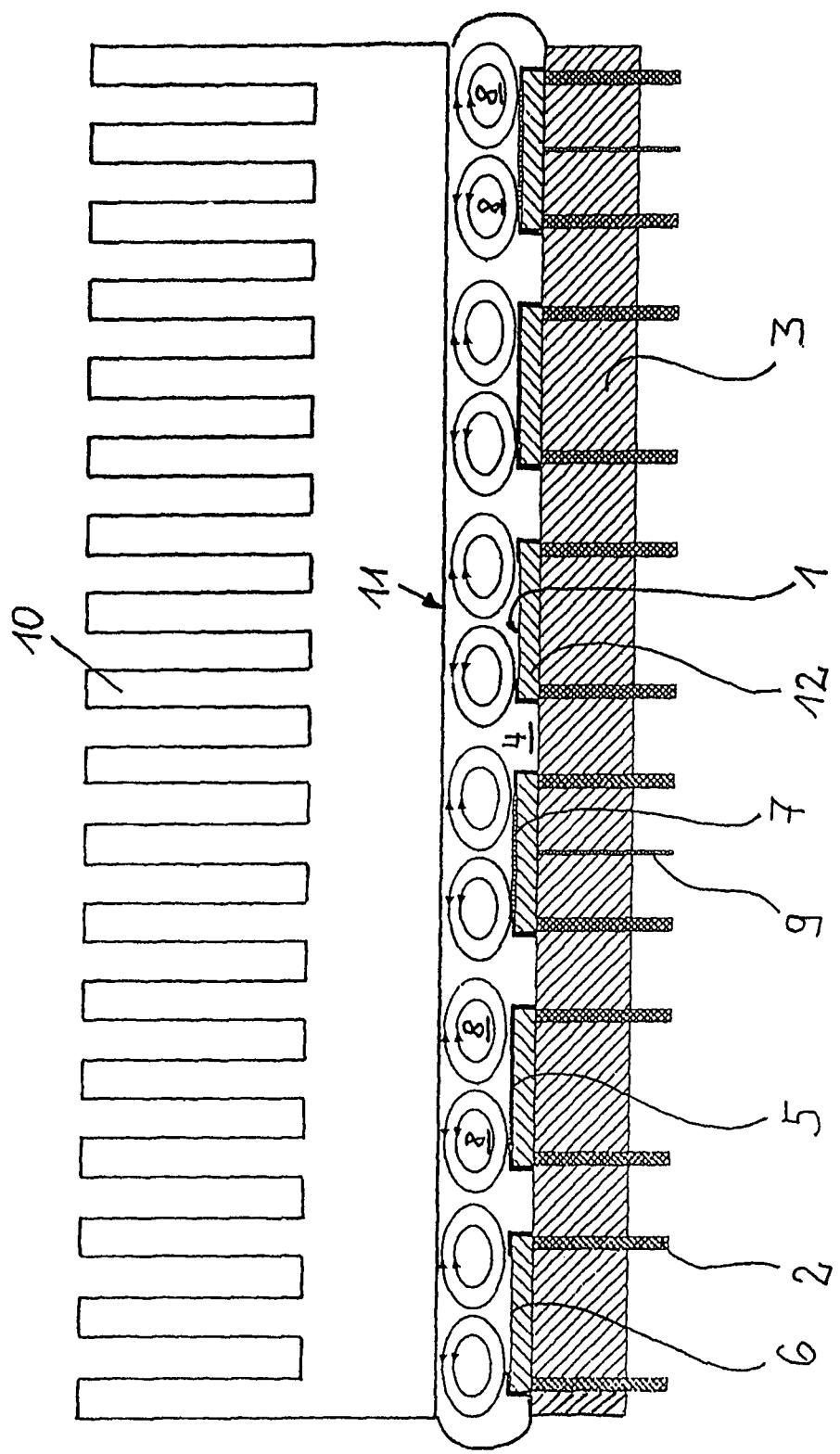
FIG. 1 is a longitudinal section through the array.
Figure 2:
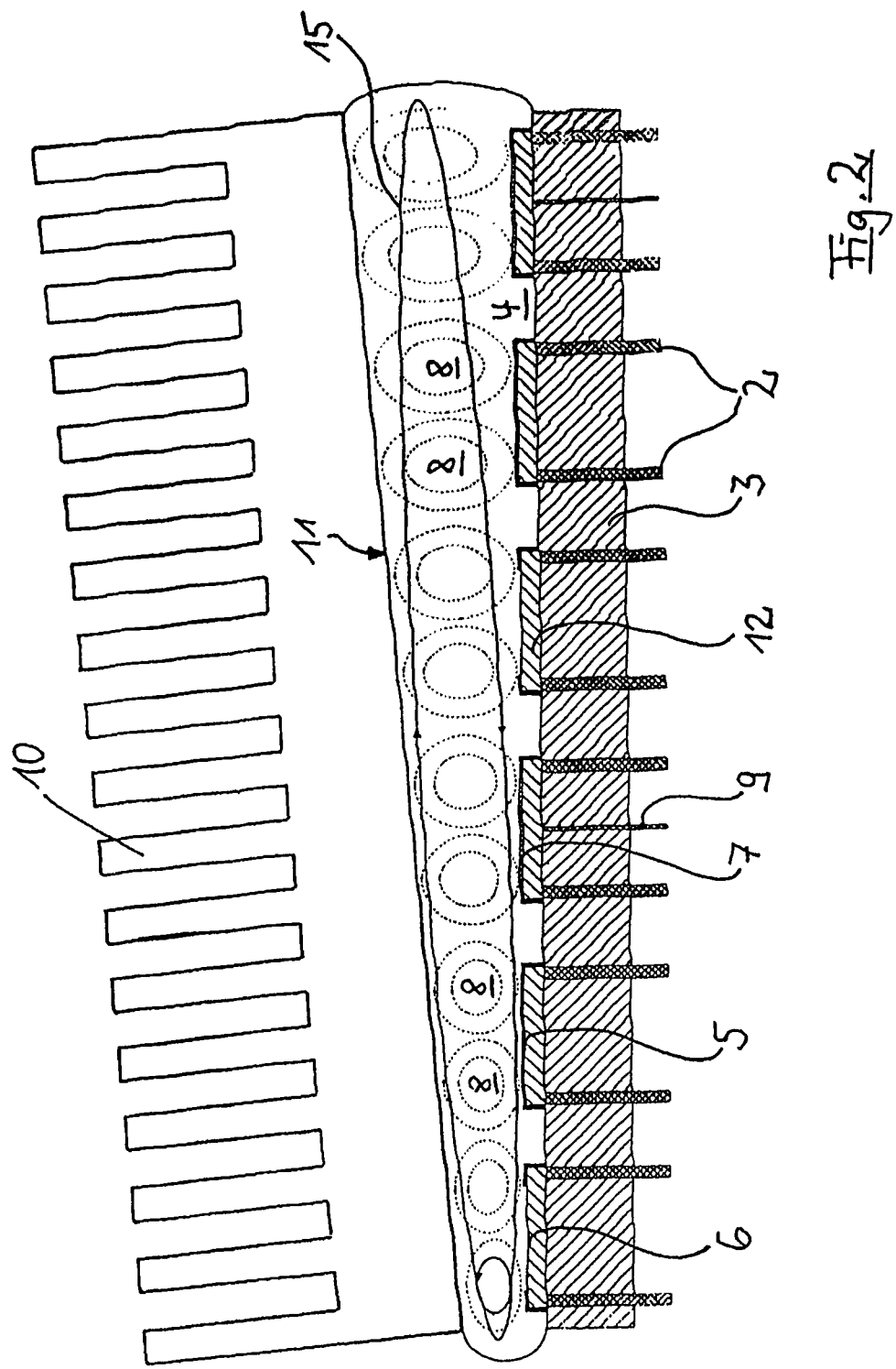
FIG. 2 is a longitudinal section through the array, with the cooling body on an incline.

FIG. 1 depicts an array with six array elements 12 that were applied to a substrate 3 for instance by sputtering. The heating current lines 2 for electrically heating the array elements 12 are conducted from both lateral ends of the array element 12 downward through the substrate 3 to a control system (not shown). A measuring contact 9 is also arranged in the center of one array element 12. The array element surfaces 1 are embodied as reaction surfaces and some are modified. While at least one array element surface 1 is embodied as a reaction surface for denaturation 6, others are fitted as an enzyme-modified reaction surface 5 or as reaction surfaces 7 modified with probe strands. The sample medium 4, which is arranged between substrate 3 and the bottom 11 of the cooling body 10 with the array elements 12 is located above the substrate 3. Separate thermal convection areas 8 that force mixing due to the turbulences that occur among them are created in the sample medium 4 above each array element 12 due to the heating of the individual array elements 12 and the cooling on the bottom 11 of the cooler 10. The arrangement in FIG. 2 is similar to that in FIG. 1, except that the surface 11 of the cooling body 10 that faces the array elements 12 is arranged on its longitudinal axis on a slight incline relative to the surface of the substrate 3 with the array elements 12. The angle of the arrangement of the surfaces relative to one another is 10° in this case.

Additional circulation 15 of the sample medium 4 is forced due to the wedge-shaped space between substrate 3 and cooling body 10.

Figure 3:
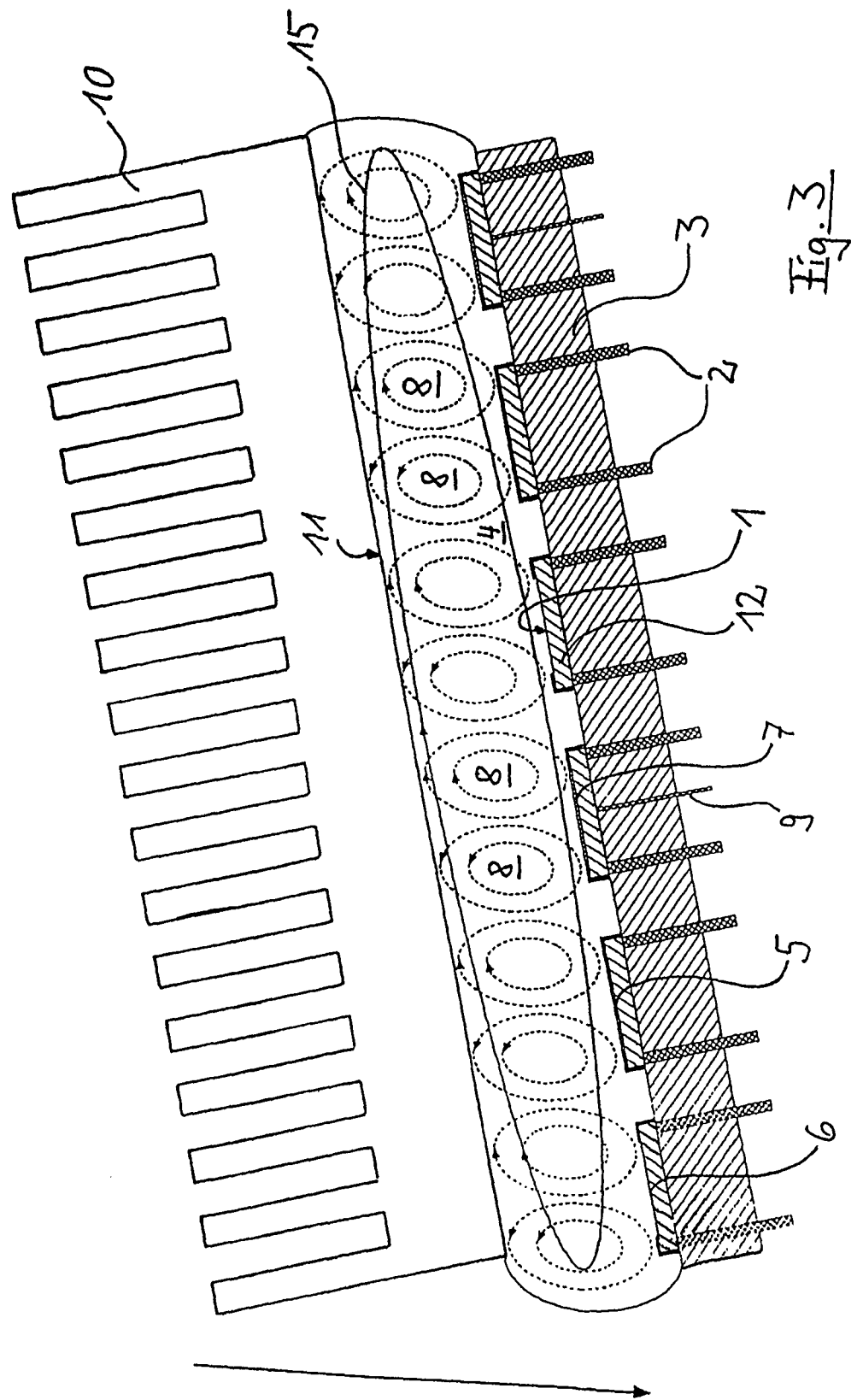
FIG. 3 is a longitudinal section through the array, which is on an incline.

In FIG. 3, the arrangement of the individual elements is the same as that in FIG. 1, except that the surfaces of the array that are adjacent to the sample medium 4 are not arranged horizontal but rather both are slightly inclined. This also forces additional circulation 15 of the sample medium 4 when the individual array elements 12 are heated.

Figure 4:
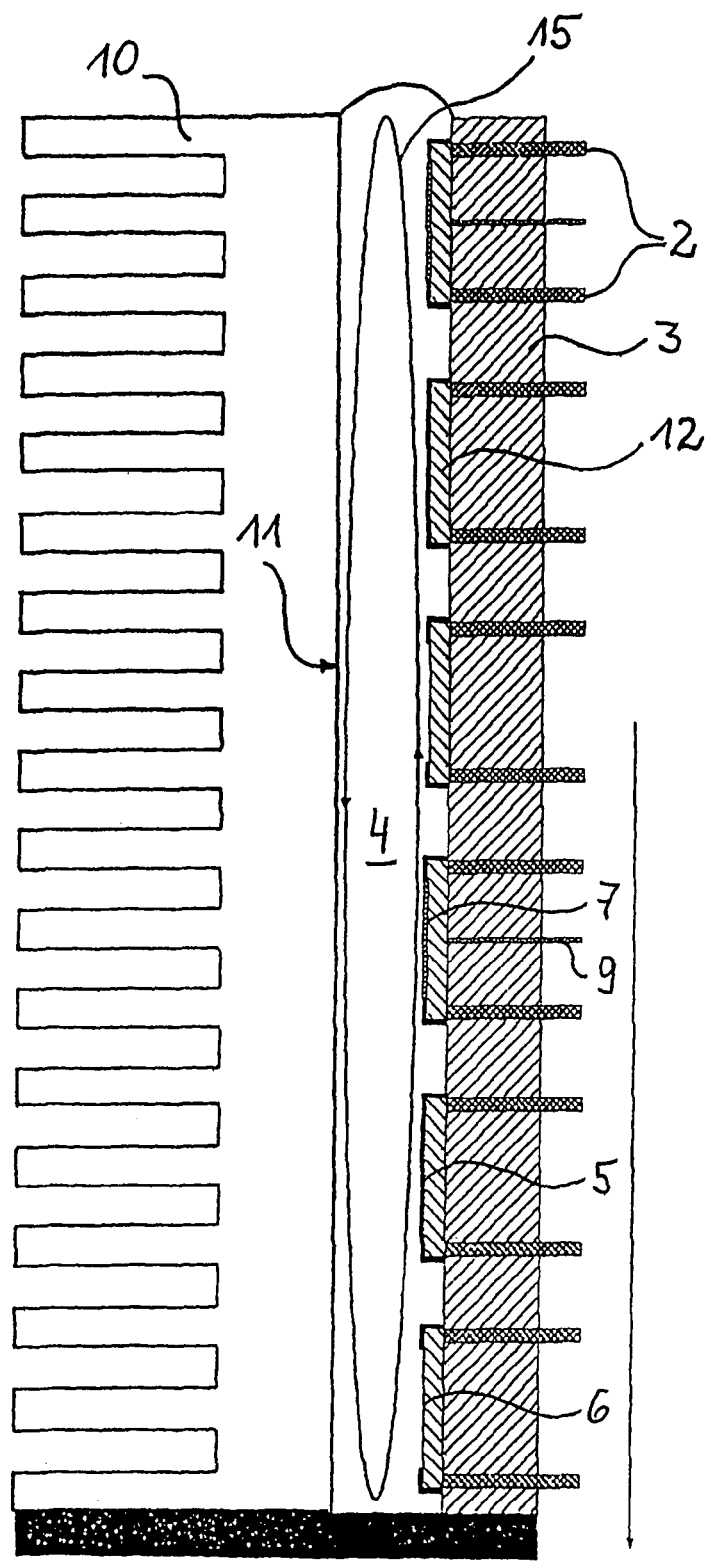
FIG. 4 is a section through the array with the surfaces of the array and cooler arranged vertically.

In contrast to FIGS. 1 through 3, in FIG. 4 the surface 11 of the cooling body 10 and that of the substrate 3, which enclose the sample medium 4, are arranged vertically. Because of this, the circulation 15 of the sample medium 4 is intensified, the sample medium 4 rising at the array elements 12 and falling at the cooling surface 11 of the cooling body 10. All of the sample medium is thoroughly mixed because of this.

Figure 5:
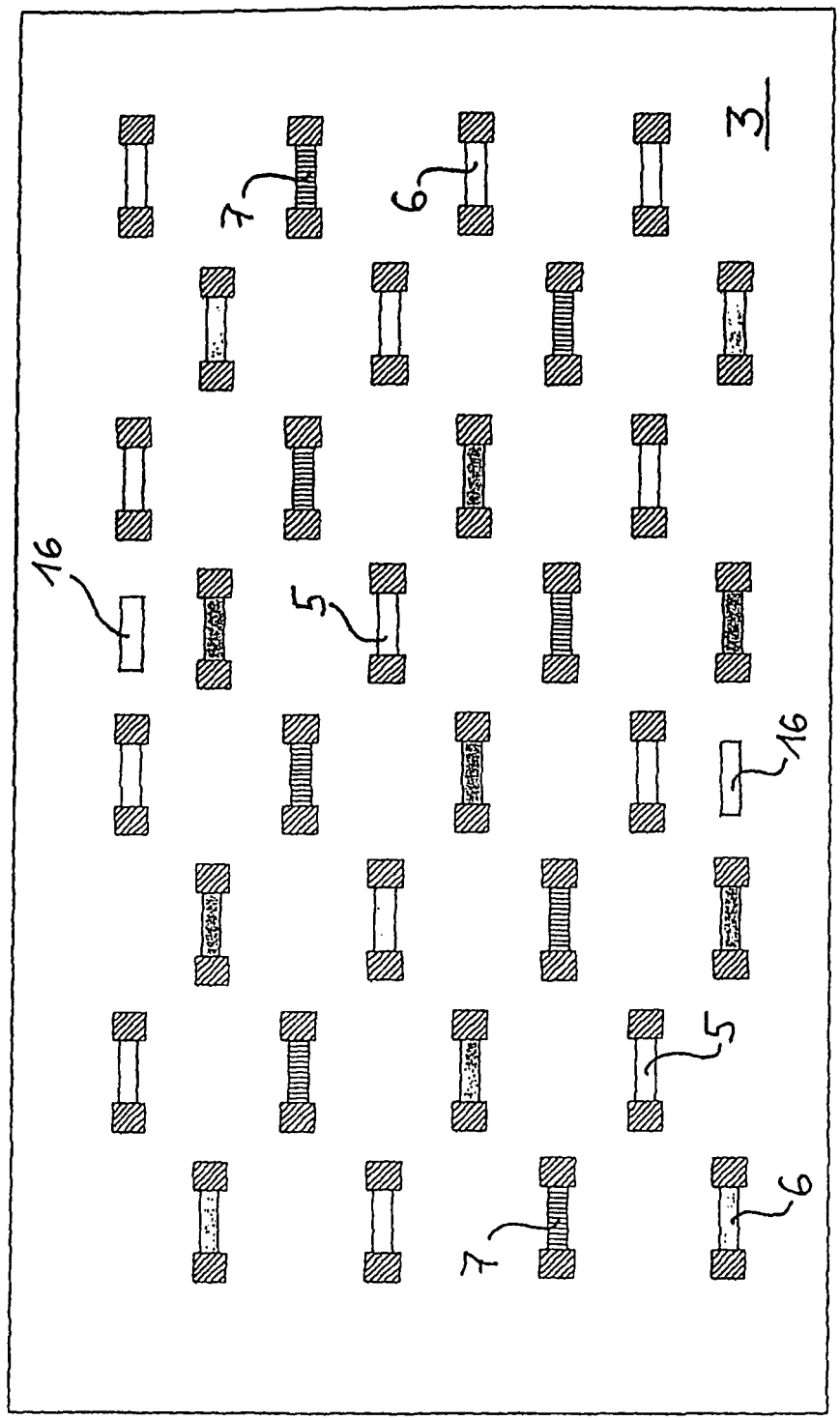
FIG. 5 is a top view illustrating the principle of the arrangement of various array elements with reference electrodes.
Figure 6:
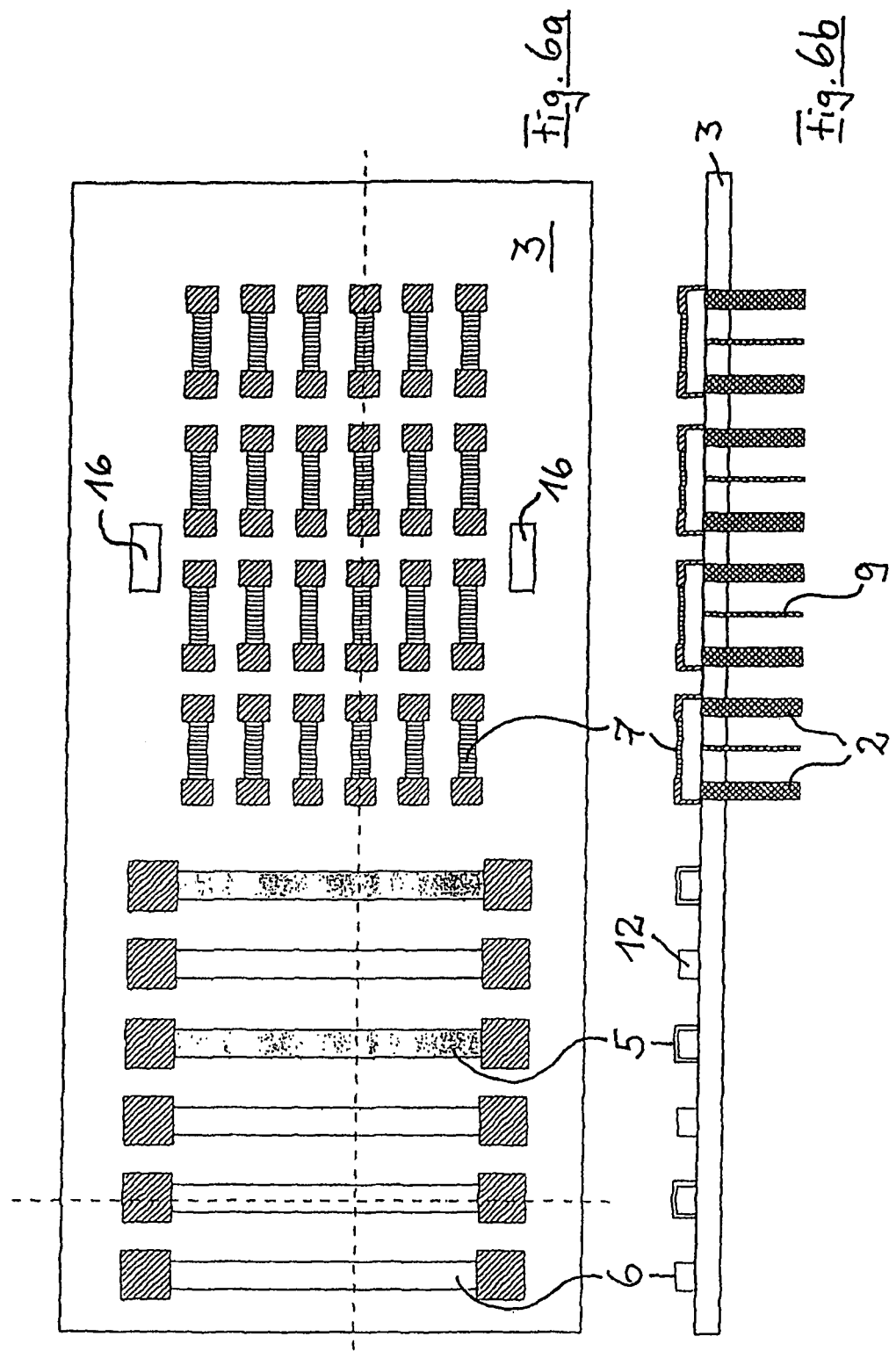
FIG. 6a is a top view illustrating the principle of the arrangement of various array elements with reference electrodes.
FIG. 6b is a cross-section illustrating the principle of the arrangement of various array elements with reference electrodes.
Figure 7:
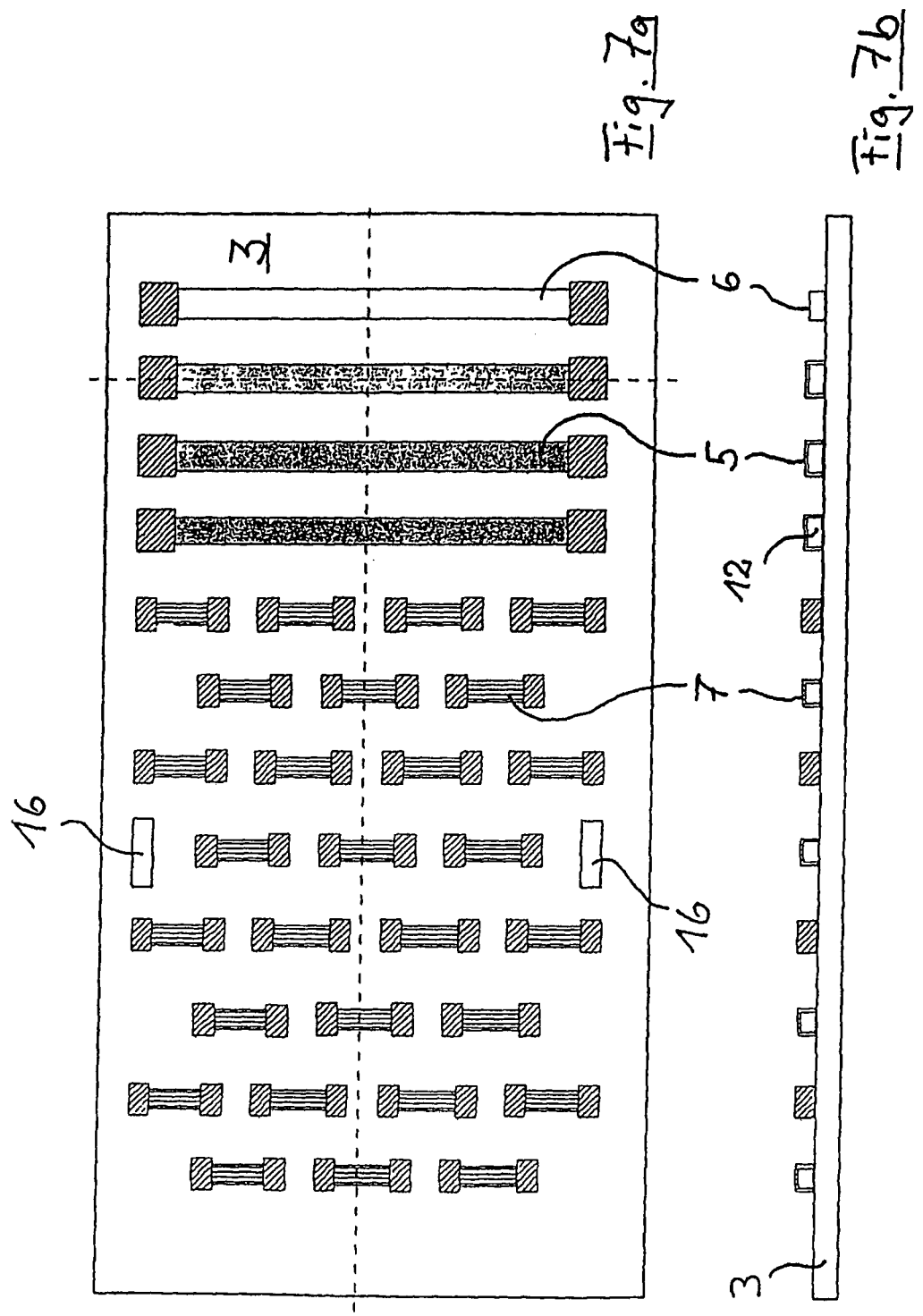
FIG. 7a is a top view illustrating the principle of the arrangement of various array elements with reference electrodes.
FIG. 7b is a cross-section illustrating the principle of the arrangement of various array elements with reference electrodes.

FIG. 5 depicts a possible arrangement in the surface of the individual enzyme-modified reaction surfaces 5, reaction surfaces for denaturation 6, and reaction surfaces 7 modified with probe strands, as well as two reference electrodes 16.

FIGS. 6a, 6b, and 7a, 7b are additional possible arrangements.

Figure 8:
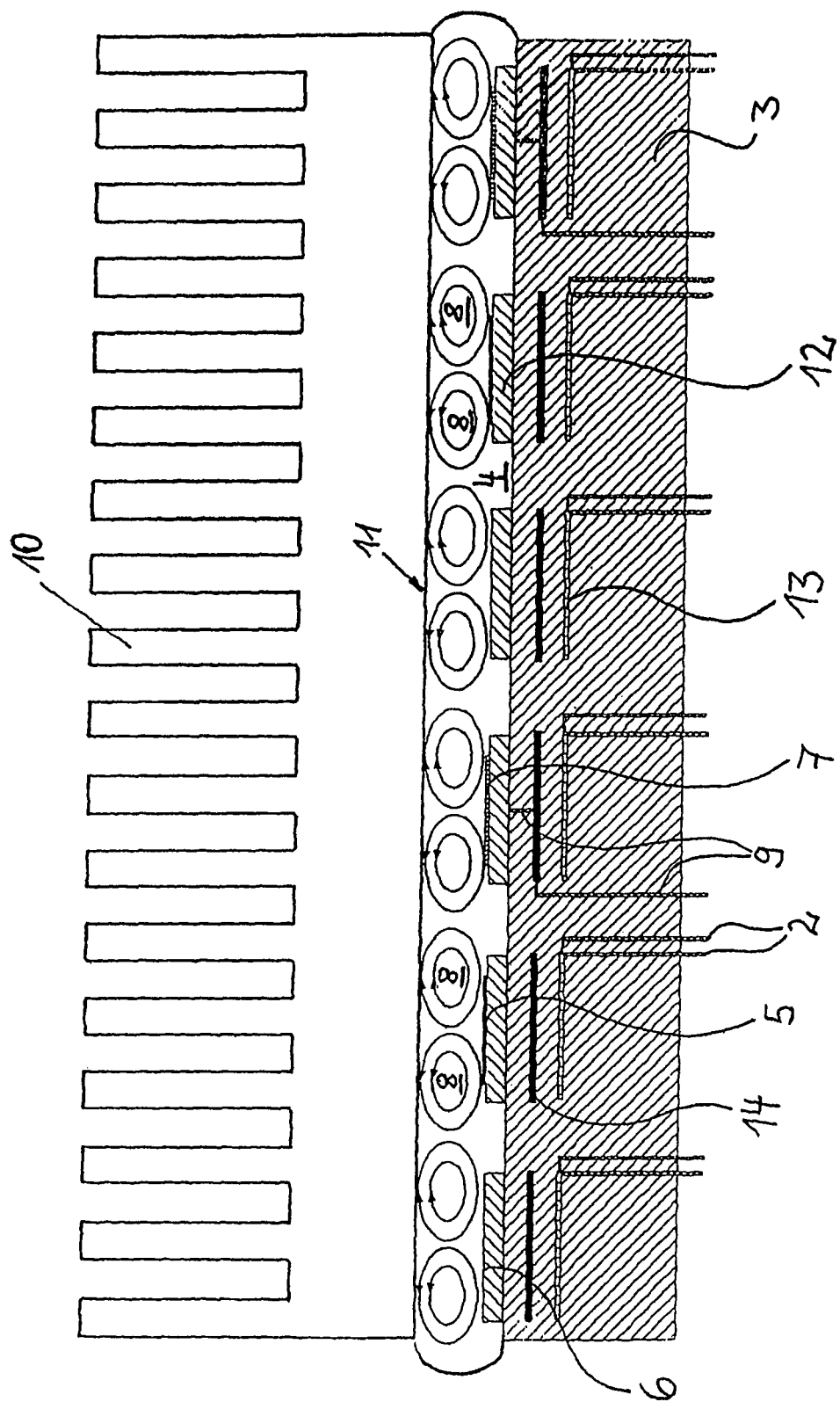
FIG. 8 is a longitudinal section through the array with indirect heating.

FIG. 8 depicts an array with indirect heating in the substrate 3. The heating elements 13 are arranged beneath the individual array elements 12, silver surfaces 14 being arranged for better and more uniform heat transmission.

FIG. 9a depicts details in the cross-section of the substrate 3, the structure and arrangement with indirect heating. A measuring contact 9 runs from the array element 12 over the silver surface 14 that is arranged beneath the array element 12. The heating element 13 and its heating current lines 2 are themselves located beneath the silver surface 14. FIG. 9b depicts the individual layers (planes A-B, C-D, E-F, and G-H) of FIG. 9a in the surface in an exemplary manner.

EXAMPLE 1

PCR, Directly Heated Array Elements, as Depicted in FIG. 1

A sample solution contains nucleic acid molecules with different genes and their sequences.

The object is to identify these genes using the short target sequences contained therein and to detect them molecularly by means of hybridization with complementary probe sequences and reporter sequences. The initial concentration is too small for a direct determination so that the target sequences must first be replicated.

A plurality of array elements 12 and their reaction surfaces 5, 6, and 7 made of gold are applied to a substrate 3, in this example made of glass, using vapor deposition. The heating current line 2 is supplied at each end of the array element 12. The contacts are conducted downward through the glass substrate. The sample solution 4 is in the form of a thin layer between the carrier 3 and a ribbed cooling body 10 made of copper with a planar gold-plated bottom 11. The latter also acts as a common counterelectrode for all array elements 12 that function as working electrodes. The surfaces 1 of the array elements 12 are embodied differently as reaction surfaces 5, 6, and 7. Thus there are three types of reaction surfaces.

The first type of reaction surface is not necessarily modified with other substances. This preferably unmodified reaction surface 6 is for denaturing the nucleic acids and is heated to a temperature greater than 90° C.

The second type of reaction surface comprises gold and is provided with a polymerase layer. Polymerase molecules are preferably chemisorbed to the gold on this reaction surface 5 via a thiol linker. Here the primer is extended at the optimum temperature for the polymerase; when using a Taq polymerase it is generally 60 to 70° C., and for most other polymerases it is 20 to 49° C. For each target sequence the sample solution contains a matching primer pair for the specific replication of the target strands. The annealing of the primer onto the target strands to be replicated occurs primarily in the vicinity of the cooling body 10.

The third type of reaction surfaces 7 is modified for hybridization with probe strands that are bonded to the gold of the array element surface 1 via thiol linkers. These array elements act as working electrodes. They possess a symmetrically arranged third contact 9 for connecting to the electrochemical measuring device. This arrangement, together with the use of alternating heating current with a 100-kHz frequency, permits simultaneous heating and measurement. The replicated target strands are detected in real time using hybridization with the matching probe and reporter strands and using electrochemical analysis of the redoxactive markings of the reporter strands, preferably using voltammetry or chronocoulometry via the measuring contact 9. The different target strands are detected using discrete complementary probe strands that are immobilized on discrete reaction surfaces 7. The known electrochemical methods for detecting the known electrochemical methods for detecting [sic] hybridization are used that for instance work with the marking of the target or reporter strands by means of iron or osmium complexes or with one or a plurality enzyme markers. By adjusting the temperature individually using regulating devices (not shown in the example) it is possible to attain optimum stringency that permits for example detection of base mismatches.

The heated reaction surfaces cause strong thermal convection in the liquid with the sample medium 4 and thus cause intensive mixing thereof. PCR processes and hybridization are accelerated because of this.

EXAMPLE 2

PCR, Indirect Heating, FIGS. 8 and 9

A sample solution contains nucleic acids having different genes and their sequences. The object is to identify these genes using the short target sequences contained therein and to detect them molecularly by means of hybridization with complementary probe sequences and reporter sequences. The initial concentration is too small for a direct determination so that the target sequences must first be replicated.

A plurality of array elements 12 and their reaction surfaces 5, 6, and 7 made of gold are applied to a substrate 3, in this example made of ceramic, using vapor deposition. The array elements are heated using heating elements 13 housed within the substrate. The silver surface 14 between array element 12 and heating element 13 distributes the heat uniformly. The conductors or heat current lines 2 are conducted downward through the ceramic substrate. The sample solution 4 is in the form of a thin layer between the substrate 3 and a ribbed cooling body 10 made of copper and having a planar gold-plated bottom 11. The latter also acts as a common counterelectrode for all working electrodes 12 in the array. The surfaces 1 of the array elements 12 are modified differently as reaction surfaces 5, 6, 7. Thus there are three types of reaction surfaces.

The first type is not modified. This unmodified reaction surface 6 is for denaturing the nucleic acids and is heated to a temperature greater than 90° C.

The second type is provided with a polymerase layer. The enzyme molecules of the polymerase-modified reaction surface 5 are chemisorbed to the gold of the array element surface 1 via a thiol linker. Here the primer is extended at the optimum temperature for the polymerase, when using a Taq polymerase it is generally 60 to 70° C. The annealing of the primer onto the target strands to be replicated occurs primarily in the vicinity of the cooling body 10.

The third type of reaction surfaces 7, the DNA-modified reaction surfaces 7 for hybridization, is modified with probe strands that are bonded to the gold of the array element surface 1 via thiol linkers. These array elements act as working electrodes. They possess a contact 9 for connecting to the electrochemical measuring device.

The replicated target strands are detected in real time using hybridization with the probe and reporter strands and using electrochemical analysis, preferably using voltammetry or chronocoulometry via the measuring contact 9. The different target strands with different target sequences are detected using discrete complementary probe strands that are immobilized on discrete reaction surfaces 7. By adjusting the temperature individually using regulating devices (not shown in the example) it is possible to attain optimum stringency that permits for example detection of base mismatches.

The heated reaction surfaces cause strong thermal convection in the liquid with the sample medium 4 and thus cause intensive mixing thereof. PCR reaction and hybridization are accelerated because of this.

EXAMPLE 3

SDA, Directly Heated Array Elements

A sample solution contains nucleic acids having different genes and their sequences. The object is to identify these genes using the short target sequences contained therein and to detect them molecularly by means of hybridization with complementary probe sequences and reporter sequences. The initial concentration is too small for a direct determination so that the target sequences must first be replicated.

A plurality of array elements 12 and their reaction surfaces 7 made of gold are applied to a substrate 3, in this example made of glass, using vapor deposition. The heating current line 2 is supplied at each end of the array element 12. The contacts are conducted downward through the glass substrate. The sample solution 4 is in the form of a thin layer between the substrate 3 and a ribbed cooling body 10 made of copper and having a planar gold-plated bottom 11. The latter also acts as a common counterelectrode for all working electrodes 12 in the array.

Strand displacement amplification (SDA) occurs in the sample solution 4. For this, the solution contains DNA strands with the target sequences to be replicated, the matching primary pairs, the polymerase, the nick enzyme, and the nucleotides in a Tris buffer at pH 8. In addition, the solution contains the reporter strands with their redoxactive markings.

The DNA-modified reaction surfaces 7 for hybridization are modified with probe strands that are bonded to the gold of the array element surface 1 via thiol linkers. These array elements act as working electrodes. They possess a third contact 9, arranged asymmetrically, for connecting to the electrochemical measuring device. This arrangement, together with the use of alternating current at the 100-kHz frequency, enables simultaneous heating and measurement. Here the replicated target strands are detected in real time using hybridization with the matching probe and reporter strands and electrochemical analysis, preferably using voltammetry or chronocoulometry via the measuring contact 9. The different target strands are detected using discrete complementary probe strands that are immobilized on discrete reaction surfaces 7. By adjusting the temperature individually using regulating devices (not shown in the example) it is possible to attain optimum stringency that permits for example detection of base mismatches. The heated reaction surfaces cause strong thermal convection in the liquid with the sample medium 4 and thus cause intensive mixing thereof. SDA reaction and hybridization are accelerated because of this.

Terms and Legends:
1. Terms
Primary Sequence:
  Base sequence of primer
Primer:
  Short nucleic acid strand that matches the longer nucleic acid strand to be replicated (template) and is extended by the polymerase or completed matching the template.
Reporter Strand:
  Nucleic acid strand that matches a target strand and can detect the latter molecularly and that is connected to a redox marker or a fluorescence marker for detecting hybridization of target and probe strands.
Probe Sequence:
  Base sequence of a probe strand.
Probe Strand:
  Nucleic acid strand that is immobilized on a reaction surface and that matches the target strand and can detect the latter molecularly.
Target Sequence:
  Base sequence of a nucleic acid strand that is to be analyzed (target strand) and that is replicated by means of PCR or SDA for this purpose and that then during hybridization joins to the probe strand and possibly the reporter strand. See Template.
Target Strand:
  Nucleic acid strand that is to be identified in a sample and is also possibly to be quantitatively determined and that characterized by its base sequence, the target sequence.
Polymerase:
  Enzyme that can extend a primer that is bonded to a template.
PCR:
  Abbreviation for polymerase chain reaction, which comprises the steps: 1. Primer annealing to the template, generally at 40 to 50° C.; 2. Primer extension for instance using the taq polymerase at generally approx. 60 to 70° C. (many other polymerases also work at room temperature); and 3. dehybridization of the double strand form at more than 90° C. The steps are repeated and lead to exponential replication of the template.
SDA:
  Abbreviation for "strand displacement amplification", a method for replicating nucleic acids at a temperature that remains the same. Initially the primer annealing occurs on the template. Then the extension of the primers using the polymerase begins. Then additional new strands are replicated while the double strands formed are separated and the strands replicated earlier by the polymerase are displaced. This can occur for instance on a nucleic acid strand using a nick caused by a nick enzyme. The steps lead to exponential replication of the template.
Taq Polymerase:
  Polymerase of the thermophilic Taq organism that remains stable and works even at high temperatures.
Template:
  Nucleic acid strand that is to be characterized as an analyte and that during PCR and SDA acts as a template for bonding and extending the primer. See Target sequence.
2. Legends:
1 Array element surface=reaction surface
2 Heating current line
3 Substrate
4 Sample medium=sample solution
5 Enzyme-modified reaction surface
6 Reaction surface for denaturation
7 Reaction surface modified with probe strands
8 Thermal convection area
9 Measuring contact
10 Cooling body
11 Bottom
12 Array element
13 Heating element
14 Silver surface
15 Circulation
16 Reference electrode

The invention claimed is:

1. A method for replicating and electrochemically analyzing one or more different target sequences in nucleic acid samples, comprising:
  a) at the same time, conducting different reactions on an array comprising selectively heatable array elements having temperature controlled reaction surfaces while the sample solution is in contact with the array elements, whereby the conducting of the different reactions effect the replication of one or more different target sequences;
  b) conducting electrochemical analysis of the one or more different target sequences on at least one of the individually temperature-controlled reaction surfaces, the surface being modified for the molecular detection of the one or more different target sequences by hybridization with probe sequences and being connected to an electrochemical measuring device for electrochemically detecting hybridization events as a working electrode thereof, the at least one of said reaction surfaces being modified with probe sequences for molecular detection of the target sequences using hybridization, wherein the temperature of said at least one modified reaction surface is individually controlled and the array element comprising the modified reaction surface is connected, as a working electrode, to an electrochemical measuring device for electrochemically detecting the hybridization events;
  c) replication of the one or more different target sequences being carried out in the following steps:
    depositing the primer on the one or more different target sequences serving as templates;
    extending the primers by way of polymerase; and
    thermally decomposing nucleic acid double strands of the target sequences; wherein
  d) replication and electrochemical analysis are carried out in an order selected from: simultaneous with each other; first and second to each other, and in an alternating sequence with each other wherein the selectively heatable array elements having temperature controlled reaction surfaces include a first array element provided with an unmodified surface for facilitating a denaturing of a nucleic acid, the first array element heatable to greater than 90° C., a second array element provided with a surface modified with a polymerase layer for facilitating the extending of primer, the second array element heatable to a temperature of 20° C. to 70*C., and a third army element provided with a surface modified for hybridization with probe strands that are bonded to the third array element by a thiol linker to gold.

2. Method in accordance with claim 1, wherein the target sequences are replicated in the following steps:
  a. annealing primer to a template
  b. extending the primer using polymerase, and
  c. thermally splitting double strands of the nucleic acid.

3. Method in accordance with claim 1, wherein the target sequences are replicated in the following steps:
  a) annealing primer to a template,
  b) extending the primer using polymerase.

4. Method in accordance with claim 1, wherein the reaction surface of at least one of the array elements is polymerase-modified and temperature of each of the polymerase-modified reaction surfaces is controlled individually.

5. Method in accordance with claim 1, wherein temperature of at least one of the reaction surfaces is set to an elevated temperature greater than 90° C. whereby the nucleic acid double strands are denatured on said at least one reaction surface of said elevated temperature.

6. Method in accordance with claim 1, further comprising, in an initial phase of the replication of the target sequences, setting the temperature of said reaction surfaces that are modified with probe strands to greater than 70° C., whereby bonding of target strands to the probe strands is suppressed.

7. Method in accordance with claim 1, further comprising electronically regulating temperatures of the reaction surfaces of said individual array elements.

8. Method in accordance with claim 1, wherein the array elements are heated by electrical current and strength of the electrical heating current is adjusted using ohmic resistances or electronic resistances.

* * * * *